United States Patent
Makdissi et al.

(10) Patent No.: US 11,027,133 B2
(45) Date of Patent: Jun. 8, 2021

(54) ULTRA-LOW POWER RECEIVER MODULE FOR WIRELESS COMMUNICATION BY AN IMPLANTABLE MEDICAL DEVICE

(71) Applicant: CAIRDAC, Antony (FR)

(72) Inventors: Alaa Makdissi, Paris (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 98 days.

(21) Appl. No.: 16/434,167

(22) Filed: Jun. 6, 2019

(65) Prior Publication Data

US 2020/0384273 A1     Dec. 10, 2020

(51) Int. Cl.
    *A61N 1/365* (2006.01)
    *A61N 1/378* (2006.01)
    (Continued)

(52) U.S. Cl.
    CPC ....... *A61N 1/36542* (2013.01); *A61N 1/3785* (2013.01); *A61N 1/3756* (2013.01); *A61N 1/3787* (2013.01); *H01L 41/08* (2013.01)

(58) Field of Classification Search
    CPC .............. A61N 1/36542; A61N 1/3785; A61N 1/3756; A61N 1/3787; A61N 1/37211; A61N 1/37233; H01L 41/08
    See application file for complete search history.

(56) References Cited

U.S. PATENT DOCUMENTS 2,390,773 A  *  12/1945  Brinton ................ G05B 11/016
                                                     307/149
6,476,637 B1    11/2002  Brownlow et al.
(Continued)

FOREIGN PATENT DOCUMENTS

| CN | 106356924 | 3/2019 | |
|---|---|---|---|
| KR | 20180000091 | 1/2018 | |
| WO | WO-2018073814 A2 * | 4/2018 | ......... A61N 1/37211 |

OTHER PUBLICATIONS

Lee, Hae-Seung, Perrott, Michael H. "6.776 High Speed Communication Circuits, Lecture 7 High Frequency, Broadband Amplifiers". MITOPENCOURSEWARE. Feb. 24, 2005. [online], [retrieved on Oct. 23, 2020], (Year: 2005).*
(Continued)

*Primary Examiner* — Mallika D Fairchild
*Assistant Examiner* — Shreya Anjaria
(74) *Attorney, Agent, or Firm* — Steven M. Greenberg, Esq.; Shutts & Bowen LLP (57) ABSTRACT

A receiver module of an autonomous implanted capsule receives a human body communication, HBC, signal sensed by an electrode in contact with body tissues or fluids of a patient. The signal is a pulse-modulated, baseband PPM pulse signal. The receiver module comprises a non-linear LNA amplifier stage comprising a pair of complementary transistors arranged as a voltage inverter circuit with an input coupled to the modulated-input-signal collecting electrode. The amplifier stage input is polarized to an intermediate operating point voltage between a supply voltage of the complementary transistor pair and a ground voltage. The amplifier stage has a gain of at least 40 dB, a gain-bandwidth product of at least 20 MHz, and a consumption lower than or equal to 100 nW. It is followed by a downstream demodulator stage made up of a fast comparator circuit of the Threshold Inverter Quantization, TIQ, type, comprising two inverters with cascade-coupled complementary transistors, one of the inverters operating as a voltage reference and the other inverter operating as a gain booster.

14 Claims, 6 Drawing Sheets

(51) Int. Cl.
 *A61N 1/375* (2006.01)
 *H01L 41/08* (2006.01)

(56) References Cited

U.S. PATENT DOCUMENTS

| | | | | |
|---|---|---|---|---|
| 8,923,795 | B2* | 12/2014 | Makdissi | A61N 1/37288 |
| | | | | 455/343.1 |
| 9,847,765 | B1* | 12/2017 | Helm | H03F 1/342 |
| 2006/0149340 | A1 | 7/2006 | Karunasiri | |
| 2009/0075591 | A1* | 3/2009 | Murdoch | G06K 7/0008 |
| | | | | 455/41.1 |
| 2011/0133839 | A1 | 6/2011 | Brekelmans | |
| 2012/0093245 | A1 | 4/2012 | Makdissi et al. | |
| 2015/0091415 | A1* | 4/2015 | Deterre | H01L 41/1136 |
| | | | | 310/339 |
| 2015/0213180 | A1* | 7/2015 | Herberholz | H01L 21/823814 |
| | | | | 716/119 |

OTHER PUBLICATIONS

Storr, Wayne. Electronics-Tutorials [online], Dec. 16, 2010 [retrieved Oct. 28, 2020], (Year: 2010).*

Talukder, A. and Sarker, M.S. "A three-bit threshold inverter quantization based CMOS flash ADC," 2017 4th International Conference on Advances in Electrical Engineering (ICAEE), Dhaka, 2017, pp. 352-356, doi: 10.1109/ICAEE.2017.8255380. (Year: 2017).*

\* cited by examiner

ULTRA-LOW POWER RECEIVER MODULE FOR WIRELESS COMMUNICATION BY AN IMPLANTABLE MEDICAL DEVICE

BACKGROUND OF THE INVENTION

Field of the invention

The invention relates to Human Body Communication, HBC, in which the communication is conducted through a medium consisting of the body tissues or interstitial fluids of a patient. This is in particular to make two devices implanted in a patient communicate with each other, or one or several implanted devices communicate with a master device, implanted or not, for example a master device that manages the exchange of information between several devices implanted at particular sites, and/or allows a communication with an external device such as a programmer or a monitoring device for the remote follow up of the patient.

A typical HBC communication application is communication between intracardiac capsules of the "leadless" type, which are autonomous implants of very small size locally implanted, for example inside a heart chamber, and which are devoid of any physical connection to a remote main device such as a pacing pulse generator casing. For this reason, these autonomous capsules are called "leadless capsules", to distinguish them from the electrodes or sensors arranged at the distal end of a lead, this lead being run through over its full length by one or several conductors galvanically connecting the electrode or the sensor to a remote casing connected to the opposite end of the lead, that contains various sensing/pacing circuits as well as a power supply battery for operating the whole device for its full expected lifetime.

The invention is however not limited to a particular type of capsule, nor even of leadless implant, and it is applicable as well to many other types of implantable medical devices, whatever the functional purpose thereof, cardiac or other, medical or not.

Description of the related art

US 2009/0171408 A1 (Solem), US 2017/0151429 A1 (Regnier) and WO 2018/122244 A1 (Regnier) describe various examples of intracardiac leadless capsules.

An HBC communication between two leadless capsules may be useful, in particular, to establish a "dual chamber" cardiac pacing system comprising two capsules (or more), including a ventricular capsule and an atrial capsule. The atrial capsule senses the atrial depolarizations of the sinus rhythm and the ventricular capsule (as well as optionally the atrial capsule) applies to the ventricle (and to the atrium) pacing pulses which are timed in order to accurately control the atrioventricular pacing delay. It is also possible in the same way to provide biventricular pacing (so-called cardiac resynchronization therapy, CRT), or to drive a subcutaneous implantable cardioverter-defibrillator (ICD) controlled by signals sensed by one or several endocavitary leadless capsules.

HBC communication applied to leadless implants is disclosed in particular by U.S. Pat. No. 8,788,035 B2 (Jacobson), U.S. Pat. No. 8,923,795 B2 (Makdissi), or by US 2016/067490 A1 (Carry) that more particularly describes a dual-chamber pacing system with two leadless implants synchronized to each other, one of which being is implanted in the ventricle and the other in the atrium of the myocardium.

A major problem in the implementation of leadless implants is their electric autonomy, and consequently the energy consumption of their circuits.

Taking into account the lifetime of such an implant, usually 8 to 10 years, and its very small dimensions it is generally not possible to use a conventional battery, even a high-density one. For that reason, these implants include a self-powering system comprising a mechanical energy harvesting device associated with a built-in temporary energy storage component, such as a rechargeable battery or a high-performance capacitor. The energy harvesting device, also known as harvester or scavenger, collects mechanical energy resulting from various movements undergone by the body of the implanted device The movements may originate from a number of phenomena occurring for example at the heartbeat rhythm, such as periodic movements of the wall on which the implant is anchored, vibrations of the cardiac tissues linked i.a. to closings and openings of cardiac valves, or blood flow rate variations in the surrounding environment, which shakes the implant and make it oscillate at the rhythm of the flow rate variations. The mechanical energy collected by the harvester is converted into electrical energy by means of a suitable mechanical-electrical transducer, for powering the various circuits and sensors of the device and for charging the energy storage component. This self-powering system allows the device to operate in full power autonomy during its full lifetime.

WO 2019/001829 A1 (Cairdac) describes an example of intracardiac leadless capsule provided with an energy harvesting device of the Piezoelectric Energy Harvester, PEH, type, which uses as a mechanical-electrical transducer an oscillating piezoelectric beam coupled to an inertial mobile mass.

To increase the autonomy of the capsule, it is essential to reduce the consumption of all the modules contained in the leadless capsule, and in particular that of HBC transmitter/receiver (TX/RX) circuits when the capsule is provided with such circuits.

A significant factor that tends to strongly increase the consumption of these TX/RX circuits is the need, in a system having several capsules communicating with each other (including, for example, an atrial capsule and a ventricular capsule), to operate the communication—and hence the activation of the TX and RX circuits—at each cardiac cycle, and even almost permanently as regards the receiver module. This is necessary for being able, for example, to detect an arrhythmia—which may occur at any moment of the cardiac cycle—in order to apply a suitable real time therapy or to ensure a good atrioventricular synchronization of the pacing, in which case the tolerance on the delay of transmission of the information issued by the atrial capsule (that senses the sinus rhythm) to the ventricular capsule (that applies the pacing) should not typically exceed 5 ms.

This constraint is particularly critical on the receiver side: actually, whereas the transmitter can be designed to consume energy only during the sending of data, the receiver consumes energy for the full duration of the listening, i.e. almost permanently.

Further, various factors contribute to disturb the HBC communication, so transmit power and/or receive sensitivity must be increased, with a consequence of an increased consumption of the TX/RX circuits. In practice, a very strong attenuation of the signals transiting in the body medium between the transmitter capsule and the receiver capsule is observed, typically of the order of 50 to 80 dB (300× to 10,000×).

It will also be seen hereinafter that the attenuation may increase due to a particular configuration of the capsules having to exchange information through HBC. Actually, the higher the angle between the respective axes of these capsules, the lower the signal collected on the receiver side, the worst case being when the axes of the two capsules are almost perpendicular to each other. Yet, this unfavorable configuration is quite close to that of a ventricular capsule implanted in the bottom of the right ventricle (hence roughly parallel to the heart axis) exchanging data with an atrial capsule implanted against the right atrial wall (hence roughly perpendicular to the heart axis).

Further, HBC communication must be performed using signals of relatively high frequency, typically higher than 20 kHz (frequency of a modulated carrier or harmonics of a pulse), so as not to interfere with the physiological signals propagating in the patient's organism, in particular neurologic signals and myopotentials.

Moreover, on the receiver side, the level of the HBC communication pulses collected must have a sufficient amplitude to discriminate them from the relatively high-level spurious electric signals present within the myocardium, which are liable to strongly degrade the signal/noise ratio. It is also necessary to discriminate, in order to exclude them, the pacing pulses issued by an implanted generator and applied locally to certain sites of the myocardium, which thereafter spread around the pacing site in a wider area before being substantially attenuated.

For these reasons, the receiver must have both a significant gain (to compensate for the human body attenuation) and a large bandwidth (high frequencies so as not to produce unwanted interferences). As, from the circuit electronic behavior point of view, the consumption of a receiver module is proportional to the gain-bandwidth product (GBP), these constraints will have a double negative impact on the consumption of the module.

Moreover, if, to reduce the consumption of the transmitter, very narrow pulses are generated to code the information to be transmitted, this will have a consequence of increasing the GBP, and hence the consumption of the receiver.

The choice of the modulation mode and parameters for HBC communication is hence a significant factor for controlling the energy budget of a leadless capsule, which must take into account the respective consumptions of both the transmitter module and the receiver module, whose performances are interdependent.

For the receiver, the known circuitry generally implements low noise amplifiers (LNAs), inverters or not, whose output drives a demodulator stage or a fast comparator referenced by a threshold generator.

Among circuits having the lowest consumption, the article of Patel et al., Design of Low Power Two Stage CMOS Operational Amplifier, *International Journal of Science and Research*, Vol. 2, Issue 3, March 2013, describes an amplifier having a GBP of 8 MHz consuming 16 µW. Beside insufficient GBP (8 MHz) with respect to what is required by a HBC communication as described hereinabove (typically requiring a GBP of 20 MHz), the consumption of such a known amplifier circuit (16 µW) is almost one hundred to one thousand times higher than the energy budget that can be allocated to the HBC receiver stage of a leadless capsule, whose consumption must not exceed 0.1 µW for preserving a longevity of at least 10 years, on the basis of what is allowed by the current harvesters and/or batteries.

A known technique for reducing the receiver consumption consists in powering it in "duty cycle" mode, namely from time to time. This technique is very limitative in a communication system for a dual-chamber pacemaker because it requires a permanent synchronization between the two capsules, and it introduces a latency that may not be acceptable for a therapy algorithm in which a capsule is supposed to act immediately in response to an event triggered by the other capsule.

Finally, the receiver stage must be able to correctly detect the coded HBC message received, even in presence of a significant dynamic attenuation.

Actually, the HBC communication channel is very unstable, because it depends on many permanently varying factors, such as, in particular, the acceleration and the position of each capsule. The receiver must be able to permanently adapt to these variations, in particular in case of a saturation of the LNA. Yet, most of the known amplifiers have a recovery time after saturation of the order of 0.1 ms to 1 ms. If this time period, which makes the amplifier temporarily "blind" to the received signal, exceeds the periodicity of the binary flow, the phenomenon may lead to decoding errors on the received message.

For an efficient HBC communication with, in particular, GBP constraints exposed hereinabove, the amplifier stage should have a minimum, ideally null, recovery time.

SUMMARY OF THE INVENTION

The invention proposes a HBC wireless communication system for implantable medical devices for fulfilling these various constraints, in particular a HBC receiver module for such a system, which is compatible with the consumption requirements of the current self-powered leadless capsules operating with a harvester and/or a battery, with a longevity that must typically reach 10 years.

According to the invention, the receiver module comprises at least one amplifier stage receiving a pulse-modulated input signal transmitted by human body communication and collected by an electrode of the implanted device. This amplifier stage is a non-linear stage comprising a pair of complementary transistors arranged as a voltage inverter circuit having an input coupled to the electrode collecting the modulated input signal, and the input of the amplifier stage is polarized to an intermediate operating point voltage between a supply voltage of the complementary transistor pair and a ground voltage.

According to various advantageous subsidiary features:
the intermediate operating point voltage is half the supply voltage;
the amplifier stage comprises a feedback resistor coupling to each other the input of the voltage inverter circuit and an output of the voltage inverter circuit, so as to generate the polarization of the amplifier stage input to the operating point voltage. This feedback resistor is advantageously made up of a MOS transistor, or of a plurality of series MOS transistors, coupling to each other the input and the output of the voltage inverter circuit;
the receiver module further comprises, downstream of the amplifier stage, a demodulator stage receiving as an input an output signal issued by the amplifier stage, which signal varies about the operating point voltage. The demodulator stage is advantageously a fast comparator circuit arranged so as to sense the voltage variations about the operating point voltage that result from the modulation of the modulated input signal after being amplified by the amplifier stage, and very advantageously a comparator circuit of the Threshold Inverter Quantization, TIQ, type, comprising two inverters with cascade-coupled complementary transistors, one of the inverters operating as a virtual voltage reference and the other inverter operating as a gain booster;

the receiver module further comprises, downstream of the demodulator stage, a discriminator stage comprising a pair of complementary transistors arranged as an inverter circuit adapted to discriminate among rising edges and falling edges of the signal issued by the demodulator circuit;

the receiver module comprises a plurality of similar non-linear amplifier stages, coupled in cascade, each comprising a pair of complementary transistors arranged as a voltage inverter circuit with a feedback resistor the pulse-modulated input signal transmitted by human body communication is a Pulse Position Modulation, PPM, coded baseband pulse signal;

the pulses of the pulse-modulated input signal have an amplitude between 100 µV and 10 mV and a duration lower than 5 µs, the at least one amplifier stage has a gain of at least 40 dB and a gain-bandwidth product of at least 20 MHz, and/or the at least one amplifier stage has a consumption lower than or equal to 100 nW.

The invention also relates to an implantable medical device comprising an ultra-low consumption unit for wireless human body communication, wherein the medical device comprises: at least one electrode adapted to come into contact with body tissues or fluids of a patient; a transmitter module comprising a modulator stage to generate a pulse-modulated output signal to be applied to the at least one electrode; and a receiver module comprising at least one amplifier stage receiving a pulse-modulated input signal collected by the at least one electrode. The amplifier stage of the receiver module is a non-linear stage comprising a pair of complementary transistors arranged as a voltage inverter circuit having an input coupled to the modulated-input-signal collecting electrode, and the input of the amplifier stage is polarized to an intermediate operating point voltage between a supply voltage of the complementary transistor pair and a ground voltage.

The pulse-modulated input signal is very preferentially a Pulse Position Modulation, PPM, coded baseband pulse signal.

In this case, the modulator stage of the transmitter module is advantageously a stage without oscillator, that comprises a XOR logic gate receiving, at a first input, a binary flow at the baseband frequency of the PPM signal and, at a second input, the same binary flow, inverted and delayed, and whose output is coupled to the at least one electrode.

The medical device may in particular be an autonomous implantable capsule comprising: an electronic unit including the wireless human body communication transmitter and receiver modules; an energy storage component for powering the electronic unit; and an energy harvesting module for powering the electronic unit and/or for charging the energy storage component.

BRIEF DESCRIPTION OF THE DRAWINGS

The foregoing and other objects, aspects and advantages of the invention will be better understood from the following detailed description of a preferred embodiment of the invention with reference to the appended drawings, in which the same numerals refer to identical or functionally similar features over the different figures.

DETAILED DESCRIPTION OF A PREFERRED EMBODIMENT OF THE INVENTION

An exemplary embodiment of the invention will now be described, in a particular application to an autonomous capsule of the leadless type intended to be implanted into a heart chamber.

As indicated hereinabove, this particular application is not limitative of the invention, whose teachings can be applied to many other types of implants, cardiac or not, or even of non-medical devices, since these devices implement a wireless transmission of messages with, in particular, signals of very low amplitude to be sensed, amplified and demodulated, in an environment imposing, as in the typical case of HBC communication, significant restrictions in terms, in particular, of signal attenuation and of gain bandwidth product GBP.

BACKGROUND OF THE INVENTION

Figure 1:
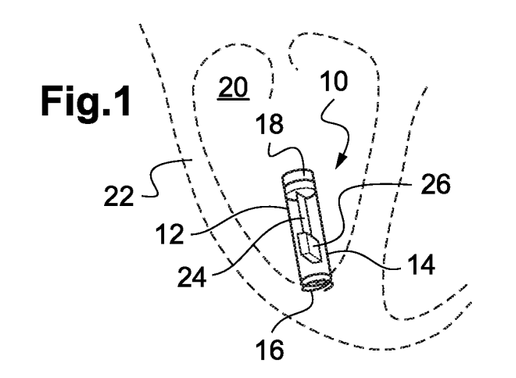
FIG. 1 illustrates a leadless capsule in its environment, implanted in the bottom of the right ventricle of a patient's myocardium.

In FIG. 1 is shown a device 10 of the leadless capsule type, in a cardiac pacing application.

The capsule 10 is in the external form of an implant with a cylindrical elongated tubular body 12 enclosing the various electronic and power supply circuits of the capsule, as well as an energy harvester with a pendular unit. The typical dimensions of such a capsule are a diameter of the order of 6 mm for a length of about 25-40 mm.

The tubular body 12 has, at its front (distal) end 14, a protruding anchoring element, for example a helical screw 16, to hold the capsule on the implantation side. The opposite (proximal) end 18 of the capsule 10 is a free end, which is only provided with means for its temporary connection to a guide catheter (not shown) or another implantation accessory for implanting or explanting the capsule.

In the example illustrated in FIG. 1, the leadless capsule 10 is an endocavitary implant implanted inside a cavity 20 of the myocardium 22, for example at the apex of the right ventricle. As a variant, still in an application to the cardiac pacing, the capsule may also be implanted on the interventricular septum or on an atrial wall, or it may be an epicardial capsule placed on an external region of the myocardium.

The leadless capsule 10 is provided with an energy harvesting module comprising an inertial pendular unit that oscillates, inside the capsule, following the various external stresses to which the capsule is subjected. These stresses may in particular result from: the movements of the wall to which the capsule is anchored, which are transmitted to the tubular body 12 by the anchoring screw 16; and/or the blood flow rate variations in the medium surrounding the capsule, which produce oscillations of the tubular body 12 at the rhythm of the heartbeats; and/or the various vibrations transmitted by the cardiac tissues. The pendular unit may in particular consist of a piezoelectric beam 24 clamped at one of its ends and whose opposite, free end is coupled to a mobile inertial mass 26, the unit forming a pendular system of the mass-spring type. Due to its inertia, the mass 26 subjects the beam 24 to a deformation of the vibratory type on either side of a neutral or non-deformed position corresponding to a stable rest position in the absence of any stress. The piezoelectric beam 24 further performs a function of mechanical-electrical transducer for converting the mechanical bending stress applied to it into electrical charges that are then collected to produce an electrical signal that, after being rectified, stabilized and filtered, will power the various electronic circuits of the capsule.

Figure 2:
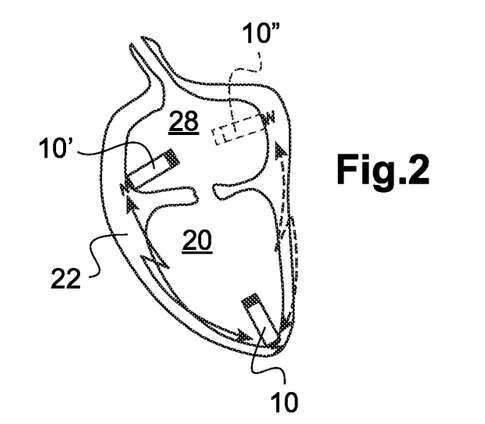
FIG. 2 schematically illustrates a myocardium with two leadless capsules communicating with each other by HBC, one capsule being implanted in the ventricle and the other in the atrium.

FIG. 2 illustrates a particular pacing configuration of the "dual chamber" type, implementing two leadless capsules 10, 10' (or 10, 10"), with one capsule 10 implanted in the right ventricle 20 (as in FIG. 1) and the other capsule 10' implanted on a wall of the right atrium 28 (or on the interatrial septum as in 10").

The two ventricular 10 and atrial 10' (or 10") capsules wirelessly communicate with each other by HBC, the communication channel then consisting of the myocardium tissues with which the electrodes of each of the capsules are in contact with at the respective implantation sites.

This implantation of two leadless capsules allows in particular a perfect synchronization of the ventricular pacing by the capsule 10 with the sinus rhythm sensed by the capsule 10', wherein the latter can also be used, if necessary, to issue atrial pacing pulses.

Figure 3:
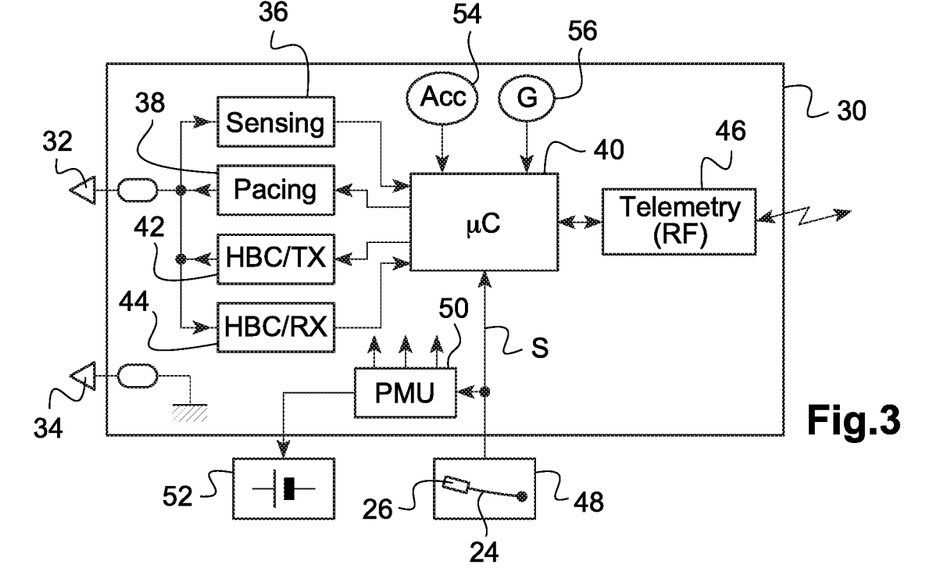
FIG. 3 schematically illustrates the main functional blocks of a leadless capsule provided with HBC communication means.

FIG. 3 is a synoptic of the various electric and electronic circuits 30 integrated to a leadless capsule provided with HBC means, shown as functional blocks. These circuits are advantageously made as an ASIC or a combination of ASICs.

Circuitry 30 is connected to electrodes 32, 34, with a sensing/pacing electrode 32 and a ground electrode 34. Electrode 32 is for example a cathode electrode located at the distal end 14 of the capsule and coming into contact with the cardiac tissue at the implantation site; as a variant, the function of this electrode 32 may be performed by the anchoring screw 16, which in this case is an electrically conductive active screw. Ground electrode 34 is for example an associated annular anode electrode, formed on the tubular body 12, in contact with the blood flow in the vicinity of the implantation site, or it may consist of the metal body of the capsule, isolated from the electrode 32.

A first function of electrodes 32, 34 is a sensing function, by collecting the cardiac depolarization potentials at the implantation site, and/or a pacing function, by applying suitable pacing pulses at this site. Electrode 32 is for that purpose connected to the input of a circuit 36 for sensing the cardiac depolarization wave, and to the output of a circuit 38 for issuing pacing pulses. Circuits 36 and 38 are connected to a microcomputer 40 that, inter alia, controls the driving of sensing/pacing functions.

A second function of electrodes 32, 34 is a HBC communication function via the communication channel consisting of the cardiac tissues and the surrounding organs or body fluids. For that purpose, electrode 32 is also coupled to the output of a HBC transmitter module 42 and to the input of a HBC receiver module 44. Modules 42 and 44 are also connected to the microcomputer 40.

The capsule also comprises a telemetry transmitter/receiver module 46, also coupled to the microcontroller and adapted to exchange signals with an external programmer or a monitoring equipment worn by the patient. This telemetry module 46, which operates in the radiofrequency (RF) band, is distinct from transmitter and receiver modules 42, 44 which are specific to HBC communication, which is a communication mode functionally different from RF telemetry.

The leadless capsule further comprises an energy harvesting circuit 48 consisting of the pendular unit formed by the piezoelectric beam 24 and the inertial mass 26 described hereinabove with reference to FIG. 1. The beam 24, which also performs a function of mechanical-electrical transducer, produces an electrical signal S that is sent to an energy management circuit 50. This circuit 50 rectifies and regulates the signal S so as to output a stabilized direct voltage for powering the electronic unit and for charging an integrated energy storage component 52, for example a rechargeable battery or a high-performance capacitor powering the electronic unit.

The leadless capsule may further be provided with sensors such as an accelerometer 54 and/or a gyrometer 56 adapted to sense and measure the instantaneous movements undergone by the capsule.

Description of a Preferential Embodiment of the HBC Transmitter

Figure 4:
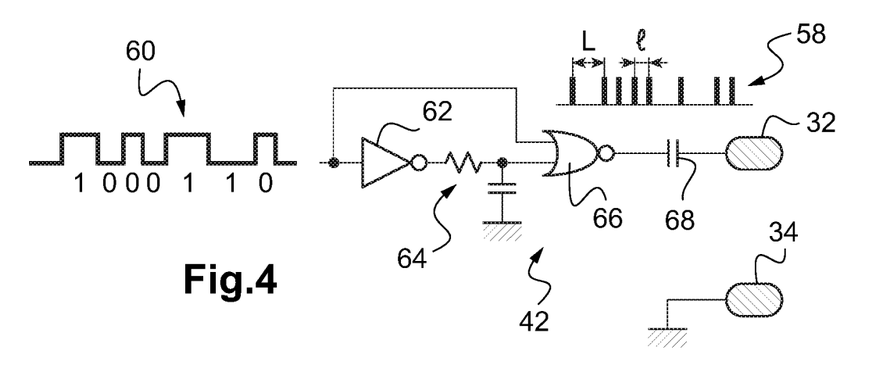
FIG. 4 illustrates the circuitry of the leadless capsule HBC transmitter module according to the invention.

FIG. 4 illustrates an advantageous preferential embodiment of the HBC transmitter module 42.

in order to reduce the energy consumption of the HBC transmitter, it is advantageous to use a communication technique of the PPM (Pulse Position Modulation) type, which is a modulation in which the '1' and '0' of the binary flow 58 are represented by intervals between successive pulses, which may take two different values L or 1. This PPM mode is a modulation operated directly in baseband, which avoids having to use a carrier frequency; it is hence not necessary to provide a fast oscillator stage, which consumes energy.

In the example illustrated in FIG. 4, the PPM pulse transmitter circuit receives as an input the binary flow 60 consisting of the alternation of the '1' and '0' of the message to be transmitted, and which is a low frequency signal liable to be generated by means of the slow clock (32 kHz) of an oscillator already available in the electronic circuits of the capsule. The binary flow 60 is applied to the input of an inverter 62, then delayed by a RC circuit 64, and the resulting signal is applied to the input of a XOR gate whose other input receives directly the binary flow 60, not inverted and not delayed. The output signal of the XOR gate 68 is applied to the electrode 32 to which it is coupled by a link condenser 68.

This structure of the HBC transmitter circuit 42 allows in particular consuming energy only during transitions, which leads to an energy consumption typically lower than 5 nW, fully compatible with energy budget and lifetime requirements specific to autonomous leadless capsules. This structure further avoids using a high-frequency oscillator to generate the narrow pulses of the PPM signal (pulses having a typical width of 1 μs).

With the consumption required to the current injected into the tissues to allow HBC communication, the total consumption of the HBC transmitter stage can be limited to about 100 nW, for an interelectrode impedance of 600-1400Ω and a pulse amplitude of 1 V.

Design Constraints of the HBC Receiver

It will now be described in detail how the HBC receiver stage 44 is made, which must fulfill a certain number of constraints linked to the HBC communication channel, while remaining in the limits of the very low power supply energy liable to be issued by an autonomous implanted capsule.

A first constraint, already mentioned hereinabove, is the necessity to have a high gain-bandwidth product GBP, herein at least about 20 MHz, to take into account both
  (i) a high maximum frequency, typically up to 200 kHz, imposed by the need, on the transmitter side, to produce very short pulses (duration lower than 5 ms) in order to reduce the average consumption on the transmitter side, and
  (ii) a significant voltage gain, on the receiver side, typically at least 40 dB, due to the attenuation introduced by the HBC communication channel, which may reach up to 80 dB in certain configurations.

As With regard to the first point, it may be pointed out that the use of very narrow pulses for HBC communication allows, as explained, reducing the consumption on the transmitter side, but that this choice has nevertheless a consequence of increasing the bandwidth, hence the GBP and consequently the consumption on the receiver side.

As regards the second point, the attenuation introduced by the HBC communication channel (which is substantially constant over the whole frequency range for the HBC communication) depends mainly on the relative position and direction of the capsules between which the messages are exchanged.

Figure 5:
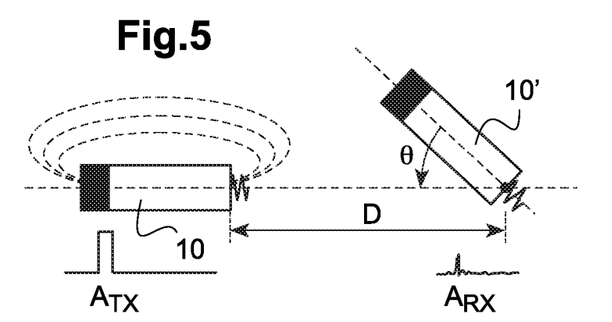
FIG. 5 explains the geometric configuration parameters that are liable to have a substantial influence on the communication channel between two capsules coupled by HBC.

More precisely, considering FIG. 5, if capsule 10 transmits a pulse of amplitude $A_{TX}$ (typically, $A_{TX}$=about 1 V, which is the minimum value for allowing a transmission by human body communication), capsule 10' will receive an attenuated and deformed pulse $A_{RX}$. In practice, for a transmitted signal $A_{TX}$=1V, the level of the corresponding pulse received does not exceed $A_{RX}$=10 mV, and can be down to $A_{RX}$=100 μV, which corresponds to a channel attenuation comprised between 40 dB and 80 dB (100× to 10,000×).

The level of the received signal depends in particular on the distance D between the capsules and on the angle θ they form to each other, the worst case being when they are directed approximately perpendicular to each other. Yet, this situation is close to the one encountered in a data exchange between a ventricular capsule and an atrial capsule, as in the configuration illustrated in FIG. 2 between capsules 10 and 10', or between capsules 10 and 10".

In order to be able to sense such short and so low-amplitude pulses, it is required to have, on the receiver side, a low noise amplifier (LNA) stage which both (i) has a high gain, typically at least 40 dB (100×) to be able to re-create pulses at an output level of at least 10 mV and (ii) is fast, i.e. having a GBP of at least 20 MHz as exposed hereinabove.

A second constraint is the necessity to reduce the consumption of the receiver module to a level comparable to the consumption of the transmitter stage, i.e. to a typical value of the order of 100 nW.

Yet, known LNAs that fulfill the first constraint exposed hereinabove (gain of at least 40 dB and GBP of at least 20 MHz) all have much higher consumptions.

For example, the above-mentioned article by Patel et al. discloses a LNA with a GBP of 8 MHz that consumes 16 μW, and other publications mention still higher consumptions.

Figure 6:
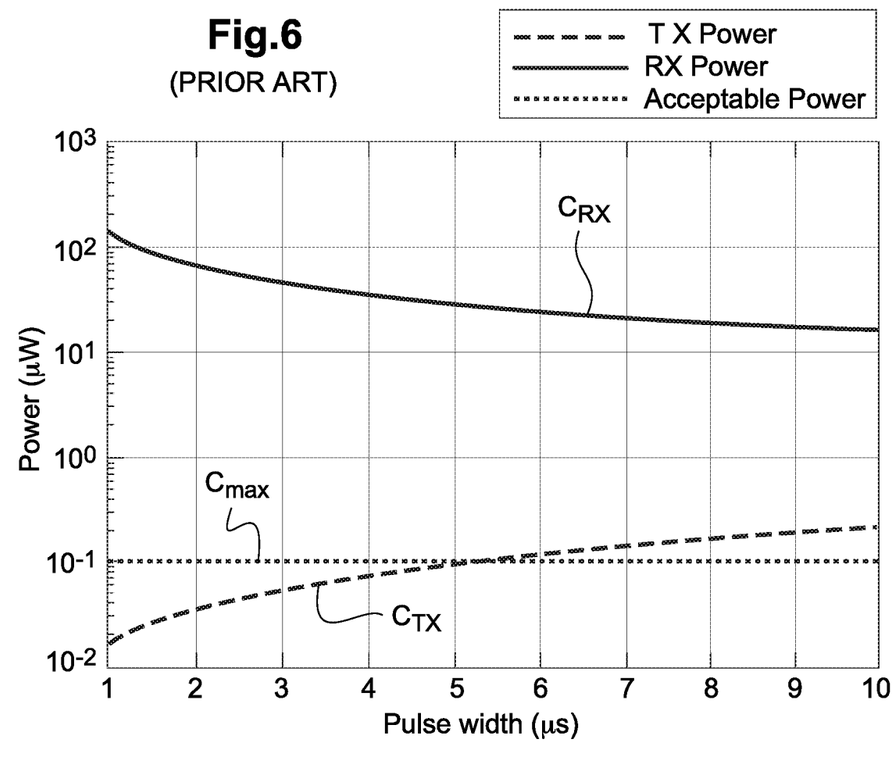
FIG. 6 is a diagram representative of the powers consumed by the transmitter and receiver stages implementing known techniques, with respect to the particular requirements specific to the leadless implants.

FIG. 6 illustrates the typical consumptions $C_{TX}$ and $C_{RX}$ of transmitter and receiver circuits described by prior art, as function of the transmitted pulse width (that determines the GBP), with respect to the acceptable limit of consumption $C_{max}$ (typically $C_{max}$=100 nW) of an autonomous implantable leadless capsule that does not penalize the capsule longevity, which must reach and exceed ten years. Concretely, it can be observed that there exists a ratio of about two to three orders of magnitude (100× to 1,000×) between what is proposed by the state of the art and what is needed to respect the consumption budget of a leadless capsule.

A third constraint is the necessity that the amplifier shows no or almost no recovery time after saturation.

This constraint is linked to the very high instability of the HBC communication channel, that generates a strong dynamic attenuation. In particular, the instantaneous acceleration, the angle and the position of the capsules vary permanently during the cardiac cycle due to the myocardium contractions and the displacements of the wall at the implantation site. Actually, the signal received at the input of the LNA, on the receiver side, will show very high and very fast amplitude variations, which are amplified in proportion by the LNA and which may cause a saturation of the output stage of this circuit.

The saturation is not per se a problem for the above-described PPM modulation, because this modulation mode does not code the information into the amplitude of the transmitted signal. However, prior art LNAs always have a recovery time after saturation, of the order of 0.1 ms to 1 ms, during which the LNA will be "deaf" to the signals received at its input. This recovery time may exceed the duration of the message bits, then leading to errors during the decoding. A remedy would consist in providing within the LNA an automatic gain control (AGC) to avoid saturation, but at the cost of an increased consumption of the amplifier stage and of a highest complexity of the circuit—hence, of a greater size on the integrated circuit, which would go against the advanced miniaturization required for a leadless capsule.

Description of Preferential Embodiments of the HBC Receiver

FIGS. 7 to 15 illustrate embodiments, given by way of example, of receiver circuits for leadless capsules fulfilling all the constraints exposed hereinabove.

Figure 7:
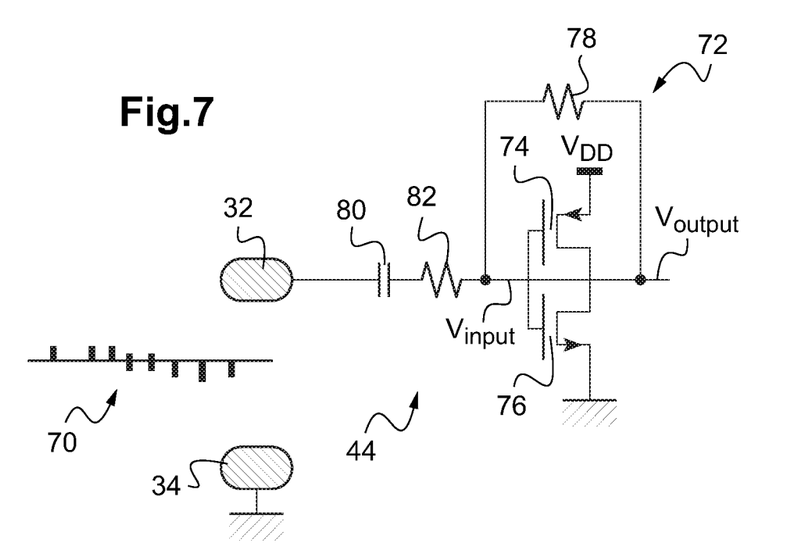
FIG. 7 illustrates the circuits of an amplifier stage of a leadless capsule HBC receiver module according to the invention.

The solution of the invention consists in making the fast LNA amplifier stage as a non-linear inverter circuit whose basic arrangement is illustrated in FIG. 7.

The HBC signal 70 collected by the electrodes 32, 34 is applied to the input of an inverter circuit 72 made up, in its simplest configuration, of two complementary transistors 74, 76, namely a PMOS 74 and a NMOS 76 coupled to each other and connected between a supply voltage source $V_{DD}$ and the ground. The input of this inverter 72 is polarized to a voltage $V_{DD}/2$ by a feedback resistor 78 coupling the input and the output of the CMOS transistor inverter. With the link capacitor 80 and the input resistor 82, the voltage of the HBC signal 70 (voltage that may be positive or negative) is hence offset to a level of the order of $V_{DD}/2$.

Figure 8:
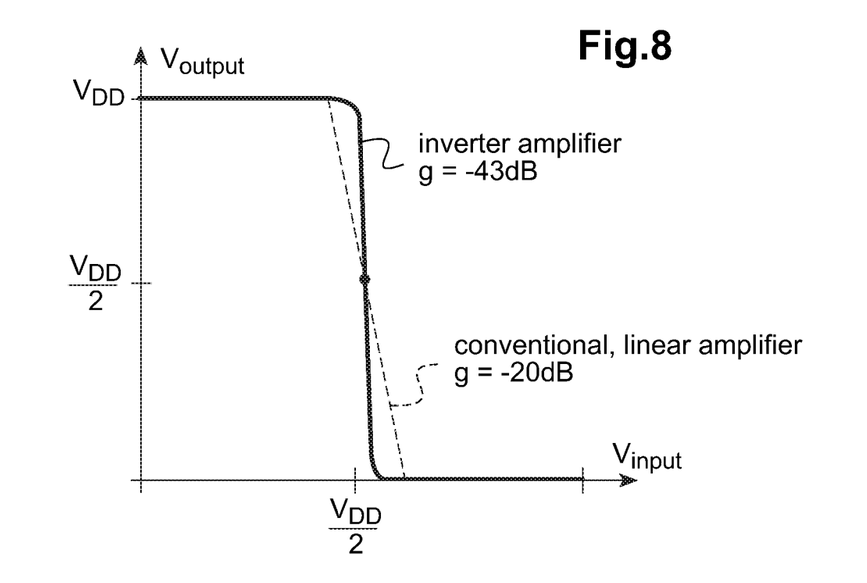
FIG. 8 is the gain characteristic of the amplifier stage of FIG. 7, compared to a gain characteristic of a conventional linear amplifier used in the same conditions.

FIG. 8 illustrates in continuous line the response of the circuit 72 of FIG. 7, which is a non-linear response: when the input signal $V_{input}$ is at a high level (corresponding to the incoming of a positive or negative pulse of the HBC signal 70), the output $V_{output}$ is almost instantaneously saturated at a voltage $V_{output}=0$ or $V_{output}=V_{DD}$; the consumption of the circuit being then reduced to an extremely low level, of the order of 100 pW.

The gain of the non-linear inverter LNA 72 corresponds to the very steep slope of the curve at the place of the transition from $V_{output}=V_{DD}$ to $V_{output}=0$. This gain, of the order of g=+20 dB to g=+40 dB according to the characteristics of the transistors that form the inverter, is to be compared to that, shown in dashed lines, of a conventional linear LNA stage, i.e. of the order of g=−20 dB. Actually, not only does the non-linear inverter LNA 72 of the invention allow significantly reducing the consumption of the circuit, but, in addition, it provides a gain that is higher than the one of a conventional linear amplifier whose gain strongly depends on the consumption.

The consumption may also be reduced with a lower supply voltage value $V_{DD}$, but at the cost of a correlative decrease of the gain.

As a variant, the CMOS transistors 74, 76 may also be controlled by a current source, instead of a voltage source $V_{DD}$.

It will be noted that the dynamic behavior of the non-linear inverter LNA 72 is independent of the level of the input signal $V_{input}$, with two significant consequences:
  i) when the collected HBC signal is a very attenuated, weak signal (having for example an amplitude of the order of 100 μV), an excellent amplification of this signal; and
  ii) when the collected HBC signal is a strong signal (having for example an amplitude of the order of 1 V), an almost absence of recovery time: that way, the LNA is not disturbed by fast changes at the level of the sensed HBC signal, which allows increasing the recurrence frequency of the pulses of the message to be transmitted without risk of information loss during the demodulation and the decoding.

Figure 9:
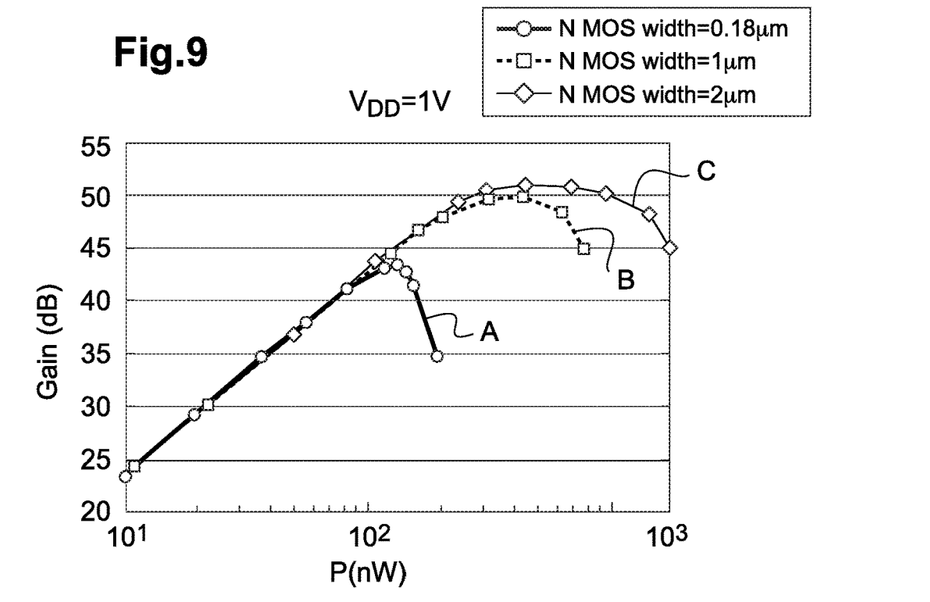
FIG. 9 is a gain-consumption characteristic for different embodiments of the amplifier stage circuit of FIG. 7.

FIG. 9 illustrates the respective characteristics A, B and C of the gain as a function of the consumption of the circuit of FIG. 7, for different dimensions of CMOS transistors 74 and 76. Actually, the consumption of the LNA 72 may be controlled by the length and width values of the transistors: hence, for a length of 1.8 μm and a width of 0.18 μm of the NMOS (characteristic A), it is possible to obtain a maximum gain of about 43 dB at 200 kHz, with a consumption of about 115 nW, for a supply voltage $V_{DD}$=1 V. To benefit from the totality of the dynamic range of the LNA, the width of the PMOS 74 is adjusted to approximately three times the width of the NMOS 76.

In any event, the cutoff frequency of the non-linear inverter LNA remains high (typically higher than 5 MHz), providing a wideband operation. In particular, if necessary, the level of consumption may be even more reduced, typically down to 20 nW, without incidence on the gain-bandwidth product GBP, which remains in the required limits exposed hereinabove (GBP of at least 20 MHz).

Figure 10:
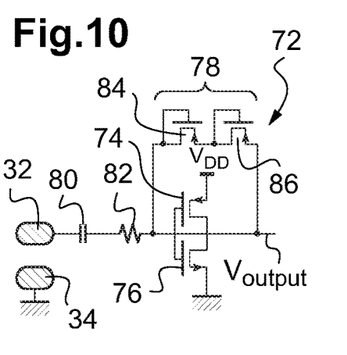
FIG. 10 illustrates a first improvement of the circuit of FIG. 7, in which the feedback resistor is made up of MOS transistors.

FIG. 10 illustrates a variant of the embodiment of FIG. 7, in which the feedback resistor 78 is made up from MOS transistors, with two PMOS 84, 86 connected in series between the input and the output of the inverter.

Since the gain of the LNA 72 is a function of the ratio between the resistances of resistors 78 and 82, the feedback resistor 78 must have a high value, typically higher than 30 MOhms. Hence, this resistor will have a relatively high area on the integrated circuit if this resistor is made as a discrete component. It is possible to reduce this area by making the resistor using a MOS technology, for example with two series PMOS of length 0.78 μm, and of width 5 to 200 μm as a function of the desired resistance value.

Figure 11:
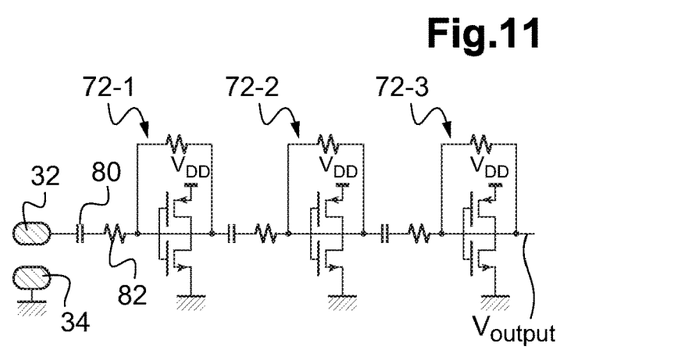
FIG. 11 illustrates a second improvement of the circuit of FIG. 7, in which a plurality of similar amplifier stages are arranged in cascade.

FIG. 11 illustrates an improvement of the circuit of the invention, that consists, to embody the non-linear LNA stage, instead of a single inverter circuit 72, a plurality of similar inverter circuits arranged in cascade, for example three inverter circuits 72-1, 72-2, 72-3 as illustrated in the figure.

Actually, it has been seen hereinabove that the gain is a non-linear function of the consumption, and that, for example, for 180 nm CMOS transistors, the highest possible obtainable gain (apex of the characteristic A in FIG. 9) is about 43 dB at 200 kHz for a consumption of 115 nW, i.e. a figure of merit of 0.37 dB/nW for a single-inverter LNA stage. If several similar inverters are arranged in cascade by modifying the length/width ratio of the transistors 74, 76 so as to maintain approximately a same components area on the integrated circuit, the gain of each inverter stage will be reduced but the overall gain of the three stages will be higher. Hence, for a same overall components area, with three inverters in cascade (configuration of FIG. 11), a total gain of 65 dB can be obtained for a total consumption of 60 nW, i.e. a figure of merit of 1.1 dB/nW.

Examples of circuits coupled downstream of the amplifier stage of FIG. 7, 10 or 11 and intended to perform the demodulation of the output signal of this amplifier stage will now be described, with reference to FIGS. 12 to 15.

Figure 12:
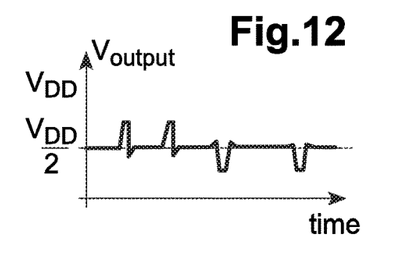
FIG. 12 illustrates an example of signal issued by the amplifier stage of a HBC receiver module according to the invention.

FIG. 12 illustrates an example of output signal of the inverter LNA stage 72 according to the invention. This signal reflects the variations of the HBC signal 70 collected through the electrodes 32, 34, in a form that is amplified and offset to a level corresponding to the polarization voltage $V_{DD}/2$. It will be noted that this amplified signal shows frequent changes of polarity about the polarization voltage $V_{DD}/2$, which correspond for example to modifications of the relative direction of the transmitter and receiver leadless capsules.

To accurately reproduce the transmitted binary flow, the output of the inverter LNA 72 is compared with a threshold voltage of a comparator stage that must: (i) have a hysteresis to eliminate the false bit detections due to the noise in the signal, (ii) be able to sense low-level pulses about the polarization voltage, to increase the dynamic range of the receiver; and (iii) have a very low consumption.

Figure 13:
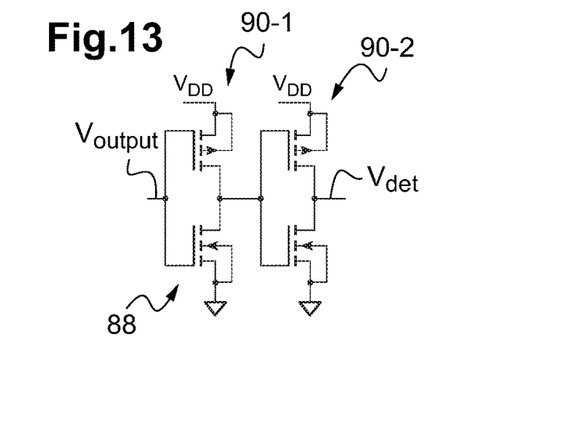
FIG. 13 illustrates a demodulator stage of the fast comparator type, coupled downstream of the amplifier stage of the HBC receiver module of the invention.

Very advantageously, the receiver module of the invention uses a fast comparator circuit of the Threshold Inverter Quantization, TIQ, type, which is a per se known circuit comprising, as illustrated by circuit 88 in FIG. 13, two inverters 90-1, 90-2 with cascade-connected complementary transistors, one of the inverters operating as a "virtual" voltage reference and the other inverter operating as a gain booster. With a very simple structure (no need of a specific generator for a reference voltage), this circuit allows sensing very low pulses about the polarization voltage $V_{DD}/2$, consumes energy only during signal transitions, and has hence only a very small incidence on the overall energy budget of the receiver module of the leadless capsule.

Figure 14:
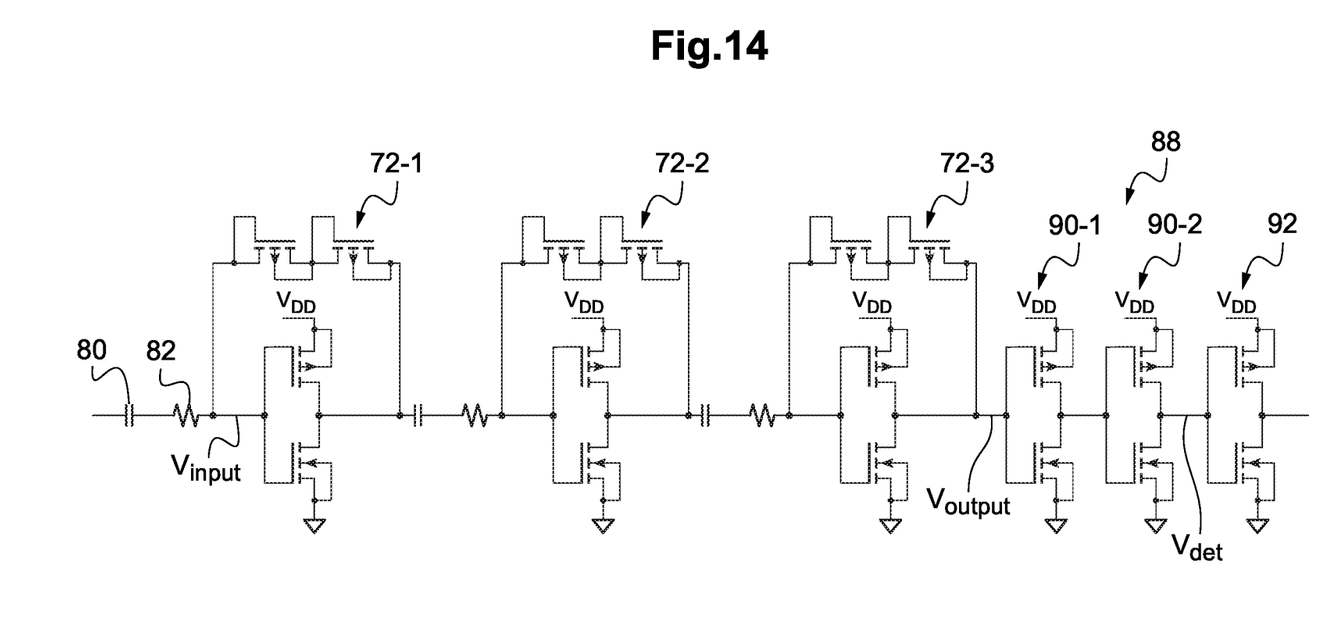
FIG. 14 illustrates a full exemplary embodiment of the circuitry of a HBC receiver module according to the invention, comprising a series of cascade-connected amplifier stages with, downstream thereof, a fast comparator demodulator stage and an edge detector stage.

FIG. 14 illustrates an exemplary embodiment of the whole HBC receiver module according to the invention, comprising, in series:

i) a first LNA stage, made up of three non-linear inverters 72-1, 72-2, 72-3 connected in cascade, as described hereinabove with reference to FIG. 11 and with feedback resistors embodied in MOS technology as described hereinabove with reference to FIG. 10;

ii) downstream thereof, a demodulator stage 88 embodied as a fast comparator of the TIQ type, with a voltage $V_{det}$ produced at an output thereof, with its two stages 90-1 and 90-2 as described hereinabove with reference to FIG. 13; and iii) downstream thereof, an (optional) discriminator stage 92 comprising a pair of complementary MOS transistors arranged as an inverter circuit, to discriminate among rising edges and falling edges of the signal issued by the demodulator circuit 88.

Figure 15:
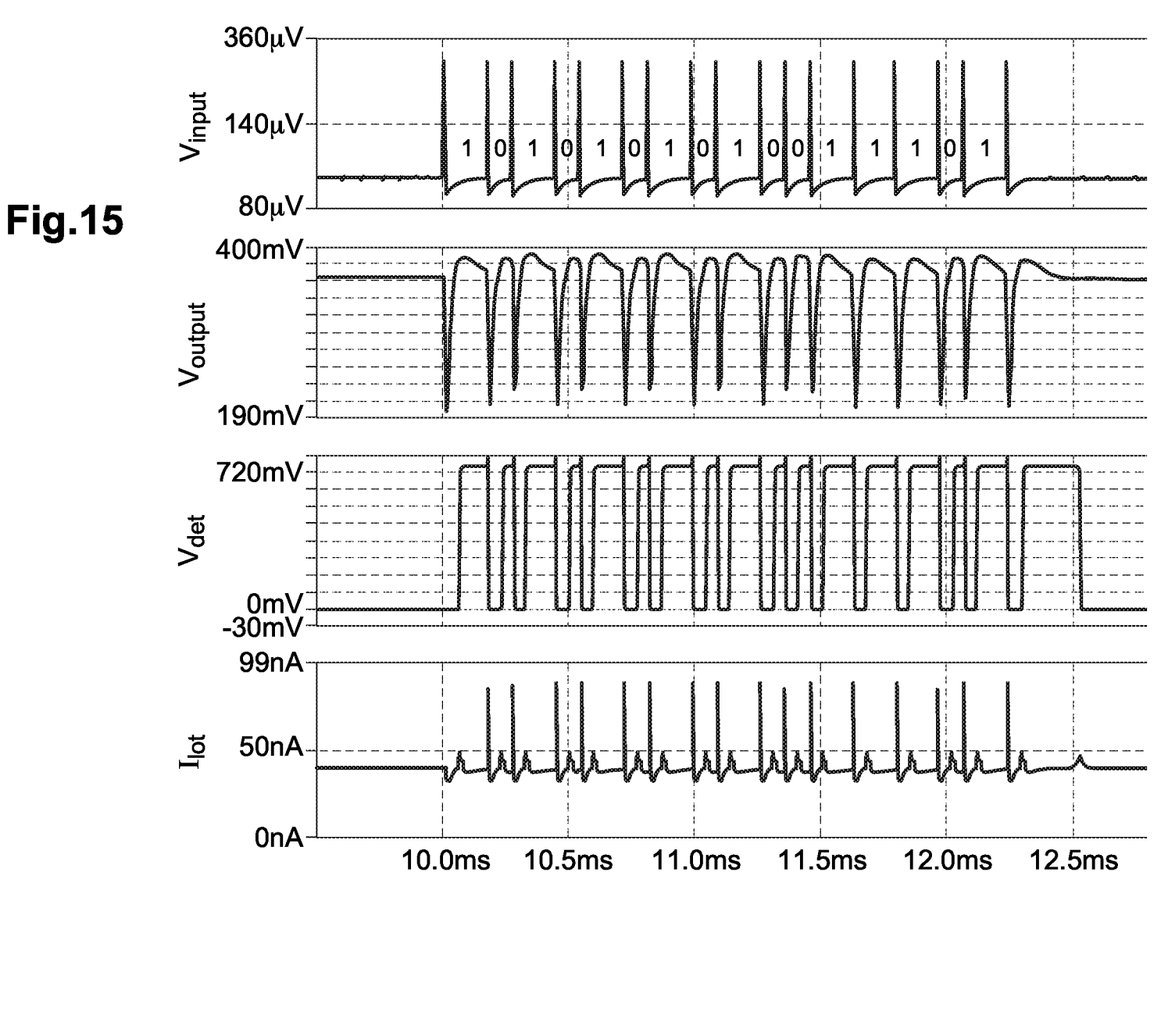
FIG. 15 is a chronogram showing the signals obtained at different levels of the circuit of FIG. 14.

FIG. 15 illustrates the different signals produced at different levels of the circuit of FIG. 14, with:

i) the signal $V_{input}$ applied to the input of the LNA stage with, for example, a succession of pulses separated by variable intervals coding the different '1' or '0' bits of the message to be transmitted and with a level of received signal $A_{RX}$ of the order of 100 µV, corresponding to a strong attenuation (of the order of 80 dB) of the HBC communication channel;

ii) the voltage $V_{output}$ issued at the output of the LNA stage consisting of the three cascade-connected inverters 72-1, 72-2 and 72-3;

iii) the voltage $V_{det}$ produced at the output of the demodulator stage made up by the TIQ comparator 88; and iv) the signal $I_{tot}$ representing the total current consumed by the circuit of the HBC receiver of FIG. 14. The average current consumed by this circuit supplied with a voltage of 1 V is about 40 nA, namely leading to an overall consumption lower than 50 nW.

The invention claimed is:

1. An ultra-low consumption wireless communication receiver module for an implantable medical device, the medical device comprising:

at least one electrode for collecting a pulse modulated input communication signal transmitted by human body communication, wherein the receiver module comprises at least one low-noise amplifier (LNA) stage receiving the modulated input communication signal and having a gain of at least 40 db and a gain-bandwidth product of at least 20 MHz, wherein the LNA stage is a non-linear stage comprising a pair of complementary transistors arranged as a voltage inverter circuit having an input coupled to the electrode collecting the modulated input communication signal, wherein the input of the LNA stage is polarized to an intermediate operating point voltage between a supply voltage of the complementary transistor pair and a ground voltage, and wherein the at least one LNA stage has a consumption lower than or equal to 100 nW.

2. The receiver module of claim 1, wherein the intermediate operating point voltage is half the supply voltage.

3. The receiver module of claim 1, wherein the LNA stage comprises a feedback resistor mutually coupling to each other the input of the voltage inverter circuit and an output of the voltage inverter circuit, so as to generate a polarization of the LNA stage input to the operating point voltage.

4. The receiver module of claim 3, wherein the feedback resistor is made up of a MOS transistor, or of a plurality of series MOS transistors, mutually coupling to each other the input and the output of the voltage inverter circuit.

5. The receiver module of claim 1, wherein the receiver module further comprises, downstream of the LNA stage, a demodulator stage receiving as an input an output signal issued by the LNA stage, which signal varies about the operating point voltage, and wherein the demodulator stage comprises a fast comparator circuit arranged so as to sense the voltage variations about the operating point voltage that result from the modulation of the modulated input communication signal after being amplified by the LNA stage.

6. The receiver module of claim 5, wherein the fast comparator circuit of the demodulator stage is a comparator circuit of the Threshold Inverter Quantization, TIQ, type, comprising two inverters with cascade-coupled complementary transistors, one of the inverters operating as a virtual voltage reference and the other inverter operating as a gain booster.

7. The receiver module of claim 5, wherein the receiver module further comprises, downstream of the demodulator stage, a discriminator stage comprising a pair of complementary transistors arranged as an inverter circuit adapted to discriminate among rising edges and falling edges of the signal issued by the demodulator circuit.

8. The receiver module of claim 1, wherein the receiver module comprises a plurality of similar non-linear LNA stages, coupled in cascade, each comprising a pair of complementary transistors arranged as a voltage inverter circuit with a feedback resistor.

9. The receiver module of claim 1, wherein the pulse-modulated input communication signal transmitted by human body communication is a Pulse Position Modulation, PPM, coded baseband pulse signal.

10. The receiver module of claim 1, wherein the pulses of the pulse-modulated input signal have an amplitude between 100 .mu.V and 10 mV and a duration lower than 5 .mu.s.

11. An implantable medical device comprising an ultra-low consumption unit for wireless human body communication, wherein the medical device comprises:

at least one electrode adapted to come into contact with body tissues or fluids of a patient;

a transmitter module comprising a modulator stage to generate a pulse-modulated output signal to be applied to the at least one electrode; and a receiver module comprising at least one low-noise amplifier (LNA) stage receiving a pulse-modulated input communication signal collected by the at least one electrode, wherein the LNA stage of the receiver module is a non-linear stage comprising a pair of complementary transistors arranged as a voltage inverter circuit having an input coupled to the modulated-input-signal collecting electrode, wherein the input and an output of the voltage inverter circuitry are mutually coupled, and wherein the input of the LNA stage is polarized to an intermediate operating point voltage between a supply voltage of the complementary transistor pair and a ground voltage.

12. The medical device of claim 11, wherein the pulse-modulated input communication signal is a Pulse Position Modulation, PPM, coded baseband pulse signal.

13. The medical device of claim 12, wherein the modulator stage of the transmitter module does not include an oscillator and comprises an XOR logic gate receiving, at a first input, a binary flow at the baseband frequency of the PPM signal and, at a second input, the same binary flow, inverted and delayed, and whose output is coupled to the at least one electrode.

14. The medical device of claim 11, wherein the medical device is an autonomous implantable capsule comprising: an electronic unit including the wireless human body communication transmitter and receiver modules; an energy storage component for powering the electronic unit; and an energy harvesting module for powering the electronic unit and/or for charging the energy storage component.

* * * * *